(12) United States Patent
Takahashi

(10) Patent No.: US 8,328,715 B2
(45) Date of Patent: Dec. 11, 2012

(54) ADAPTOR OPTICAL SYSTEM FOR ENDOSCOPES AND ENDOSCOPE

(75) Inventor: Susumu Takahashi, Iruma (JP)

(73) Assignee: Olympus Medical Systems Corp., Tokyo (JP)

( * ) Notice: Subject to any disclaimer, the term of this patent is extended or adjusted under 35 U.S.C. 154(b) by 1325 days.

(21) Appl. No.: 12/072,640

(22) Filed: Feb. 26, 2008

(65) Prior Publication Data

US 2008/0208005 A1 Aug. 28, 2008

(30) Foreign Application Priority Data

Feb. 27, 2007 (JP) ................................. 2007-047612

(51) Int. Cl.
*A61B 1/06* (2006.01)
*G02B 21/00* (2006.01)
*G02B 3/00* (2006.01)

(52) U.S. Cl. ........ 600/175; 600/160; 600/172; 359/368; 359/642

(58) Field of Classification Search ................... 600/175, 600/160, 172, 176, 166, 109, 162, 168; 356/419; 359/368, 642, 738, 739, 434, 435

See application file for complete search history.

(56) References Cited

U.S. PATENT DOCUMENTS

| | | | | |
|---|---|---|---|---|
| 4,364,629 A * | 12/1982 | Lang et al. | ..................... | 359/377 |
| 4,660,982 A * | 4/1987 | Okada | ........................... | 356/636 |
| 5,522,789 A * | 6/1996 | Takahashi | ..................... | 600/166 |
| 6,110,104 A * | 8/2000 | Suzuki et al. | ................. | 600/124 |
| 8,040,597 B2 * | 10/2011 | Sasaki | ........................... | 359/388 |
| 2002/0082476 A1 * | 6/2002 | Takahashi et al. | ............ | 600/173 |

FOREIGN PATENT DOCUMENTS

| JP | HEI 9-248276 | 9/1997 |
|---|---|---|
| JP | 2000-10024 | 1/2000 |
| JP | 2004-264835 | 9/2004 |

\* cited by examiner

*Primary Examiner* — John P Leubecker
*Assistant Examiner* — Ronald D Colque
(74) *Attorney, Agent, or Firm* — Kenyon & Kenyon LLP

(57) ABSTRACT

An optical system which can be detached and attached is constituted such that it is arranged at the object side of an objective optical system for endoscope in which an incidence pupil is arranged, and a middle image of the objective is formed at its inside, and in the arrangement state, the incidence pupil of the objective optical system for endoscope is relayed at a predetermined position which is more projected toward the utmost object side than a surface at the object side in the endoscope. (An incidence pupil which is conjugate with an incidence pupil is arranged at a position which is more projected toward the object side by a predetermined amount than a surface which is at the utmost object side in the endoscope).

6 Claims, 4 Drawing Sheets

$\omega 1 \leq \omega 1'$

ADAPTOR OPTICAL SYSTEM FOR ENDOSCOPES AND ENDOSCOPE

This application claims benefits of Japanese Patent Application No. 2007-47612 filed in Japan on Feb. 27, 2007, the contents of which are hereby incorporated by reference.

BACKGROUND OF THE INVENTION

1. Field of the Invention

The present invention relates to an adapter optical system for endoscope which is used by being arranged at the object side of an objective optical system for endoscope and an endoscope.

2. Description of the Related Art

So far, an endoscope has been used for observation of a part which is difficult to observe from the outside in cases such as a medical treatment and/or diagnosis of inside of body of a patient in the field of medicine, an inspection of inside of a pore formed in a product in the field of industry, etc.

Generally, an endoscope has an image transmission optical system, an objective optical system, a relay lens (in case of a rigid endoscope) an image guide fiber (in case of a flexible endoscope) etc., in the inside of an insertion part at a top part having a cylindrical shape with small diameter. And, it is constituted so that light which comes from an observation object and passes through these optical systems may be observed as an observation image through an eyepiece optical system or an image pick-up optical system. In a video endoscope, it is constituted that imaging elements, such as an objective optical system and CCD, are built in at the top part.

In General, an objective optical system for endoscope is constituted with what is called retro focus type, in order to satisfy requirements for small diameter of a path, and wide angle of an observation visual field, wherein in the order from an object side, it has a lens group with negative refracting power, a brightness aperture stop, and a lens group with positive refracting power, and an incidence pupil with a brightness aperture stop is arranged at the inside of it.

Such objective optical system for endoscope is shown in Publication of the Japanese unexamined patent application, Toku Kai. No. 2004-264835, Publication of the Japanese unexamined patent application, Toku Kai. No. 2000-10024, Japanese published unexamined patent application Toku Kai Hei 9-248276, etc., for examples.

In case that a diameter of a pipe is smaller than an outside diameter of an endoscope, for example, in case of a ureter, a bile duct and the likes which are connected with a kidney from a bladder in a living body as shown in FIG. 1, and in case that a diameter of a pore is smaller than an outside diameter of an endoscope in an industrial commodity, it is difficult to insert an endoscope having a diameter with general size into such pipe or pore. Use of an endoscope having especially a small diameter for inserting in a pore of a thin path with small diameter may be considered. However, since such endoscope with small diameter especially made requires a very high manufacturing cost, it is difficult to be used widely. Even if small-sizing or thinning of the diameter of an endoscope could be achieved, there is a certain limit. Thus, it is desired that pathological change and abnormality of a pipe and a side wall of a pore having a thin path with a diameter smaller than an outside diameter of the endoscope can be observed exactly to a certain extent.

However, in a constitution having an incidence pupil of an objective optical system for endoscope inside of an objective optical system for endoscope like the conventional endoscope, flux of light from an object enters into a top surface of the objective optical system for endoscope so that it may direct toward the central position of the incidence pupil.

In case that a pore having a thinner path than the outside diameter of an endoscope is observed, in order to observe an inside of the pore as much as possible, it is necessary to take a large angle of incidence of light which enters into the top surface of the objective optical system for endoscope from the side wall inside the pore as much as possible. For that purpose, it is necessary to bring the top surface of the objective optical system for endoscope close to an entrance of the pore as much as possible. However, even if it makes it such way, if the path of the pore is smaller than the path of the top surface of the objective optical system for endoscope, the light from the perimeter of the entrance of the pore in addition to the light from the side wall of the pore will enter into the top surface of the objective optical system for endoscope at a considerable rate. And, since incidence light from the smaller pore than the diameter of the objective lens has a smaller angle of incidence than the incidence light from the perimeter of the pore, an amount of information of the image obtained from the side wall of the pore becomes less.

SUMMARY OF THE INVENTION

The adapter optical system for endoscope according to the present invention is an adapter optical system for endoscope arranged at an object side of an objective optical system for endoscope in which an incidence pupil is arranged, is constituted such that an image at a middle position of the objective is formed inside of the adapter optical system, and in a state such that the adapter optical system is arranged at the object side of the objective optical system for endoscope, the incidence pupil of the objective optical system for endoscope is relayed at a predetermined position which is more projected toward the object side than a surface at the utmost object side in an endoscope in a state that the adapter optical system is arranged at the object side of the objective optical system for endoscope.

The endoscope according to the present invention comprises an objective optical system for endoscope having an incidence pupil inside, and a top part optical system which is arranged at the object side of the objective optical system for endoscope, wherein an image at a middle position is formed inside, and the incidence pupil of the objective optical system for endoscope is relayed at a predetermined position which is more projected toward the object side than a surface which is at the utmost object side in the endoscope.

It is desired that the adapter optical system for endoscope of the present invention can be detached and attached to the objective optical system for endoscope.

It is desired that the adapter optical system for endoscope of the present invention comprises a light guiding means which guides light emanated from an illumination optical system arranged around the objective optical system for endoscope to an observation object.

It is desired that in the adapter optical system for endoscope of the present invention, the top part optical system can be detached and attached to the objective optical system for endoscope.

It is desired that the adapter optical system for endoscope of the present invention further comprises a light guiding means which guides light emanated from the illumination optical system arranged around the objective optical system for endoscope to an observation object.

According to the adapter optical system for endoscope and the endoscope of the present invention, a side wall of a pipe and of the inside of a pore having a diameter thinner than the outside diameter of the endoscope can be observed with sufficient accuracy are obtained, even though a conventional constitution of the objective optical system for endoscope is used.

These and other features and advantages of the present invention will become apparent from the following detailed description of the preferred embodiments when taken in conjunction with the accompanying drawings.

BRIEF DESCRIPTION OF THE DRAWINGS

FIG. 2 is an explanatory diagram of an adapter optical system for endoscope and an endoscope concerning one of embodiments of the present invention.

FIG. 3 is an explanatory diagram in case that observing of a pore having a smaller diameter than an outside diameter of an endoscope using the endoscope having an adapter optical system for endoscope of the present invention.

FIG. 4 is an explanatory diagram in case that observing of a pore having a smaller diameter than an outside diameter of an endoscope using a conventional endoscope.

DETAILED DESCRIPTION OF THE PREFERRED EMBODIMENT

Figure 2A:
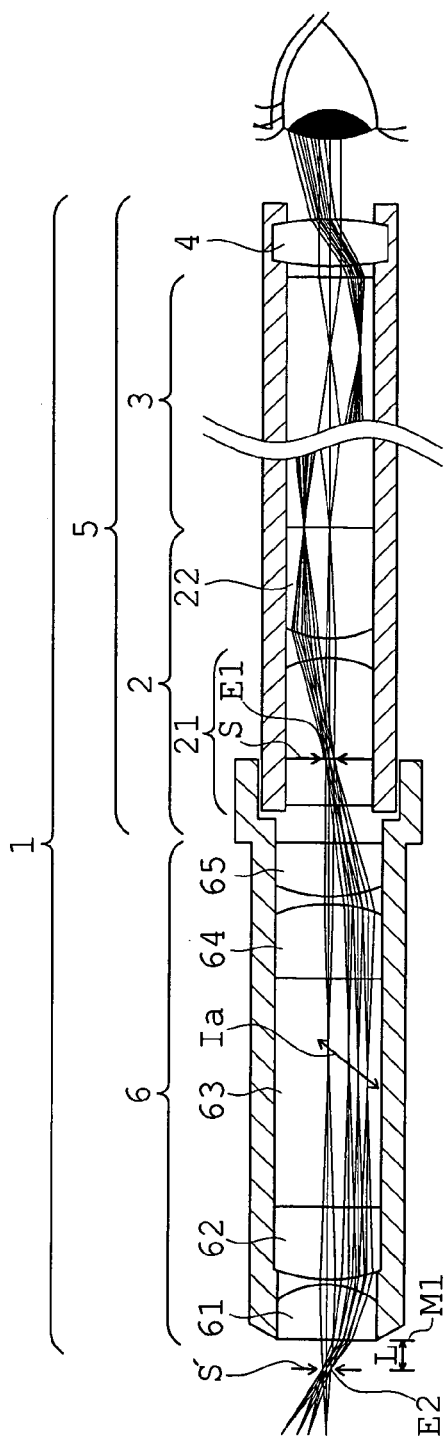
FIG. 2A is an explanatory diagram showing an outlined composition of the endoscope.
Figure 2B:
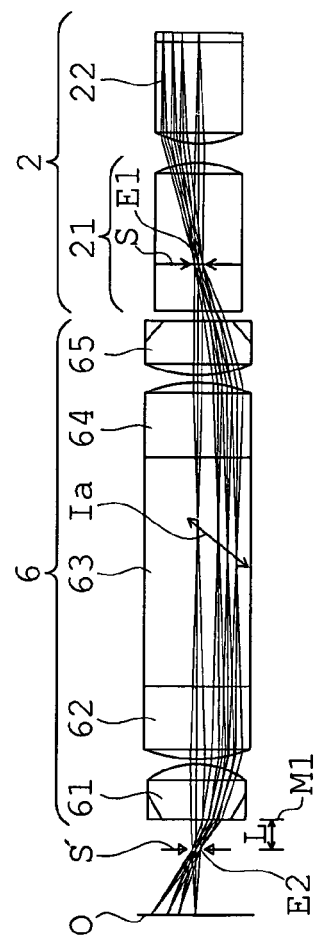
FIG. 2B is an explanatory diagram of the principal part of FIG. 2A.

FIG. 2 is an explanatory diagram of an adapter optical system for endoscope, and an endoscope concerning one of embodiments of the present invention. FIG. 2A is an explanatory diagram showing an outlined composition of the endoscope, and FIG. 2B is an explanatory diagram of the principal part of FIG. 2A.

Figure 3A:
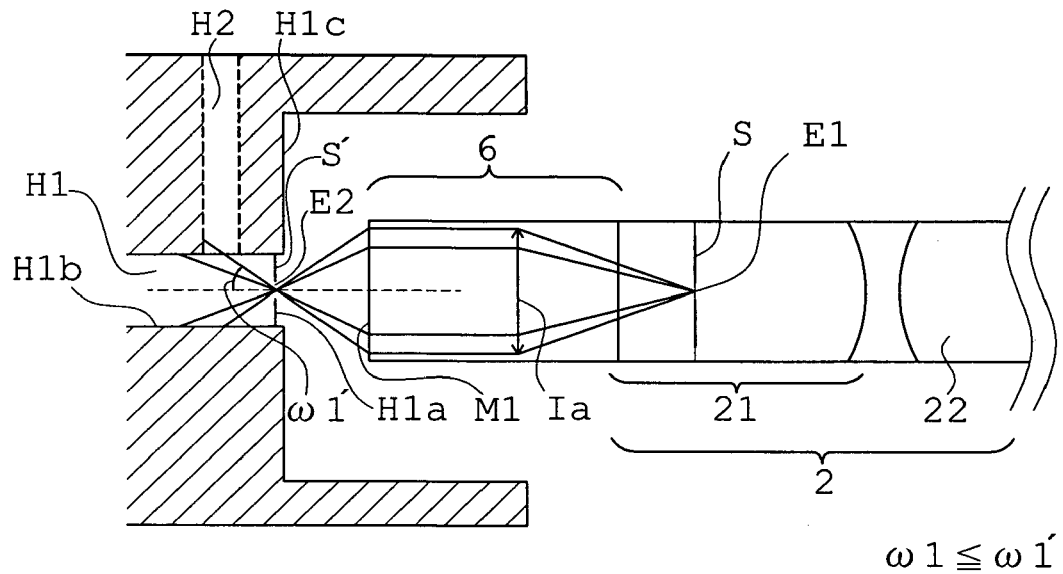
FIG. 3A is a principle diagram showing incidence light from an object conceptually.
Figure 3B:
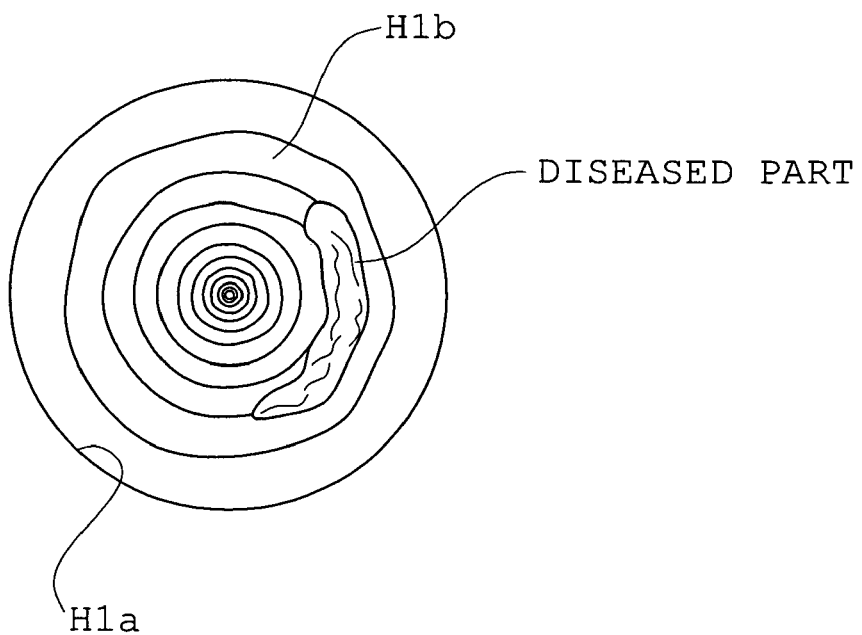
FIG. 3B is an explanatory diagram which illustrates a state of an image obtained when a pore having a smaller diameter than an outside diameter of an endoscope in a state shown in FIG. 3A.

FIG. 3 is an explanatory diagram in case that a pore having a smaller diameter than an outside diameter of an endoscope is observed by using the endoscope having an adapter optical system for endoscope of the present invention. FIG. 3A is a principle diagram showing conceptually incidence light from an object, and FIG. 3B is an explanatory diagram which illustrates a state of an image obtained when a pore having a smaller diameter than the outside diameter of an endoscope is observed in a state shown in FIG. 3A.

Figure 4A:
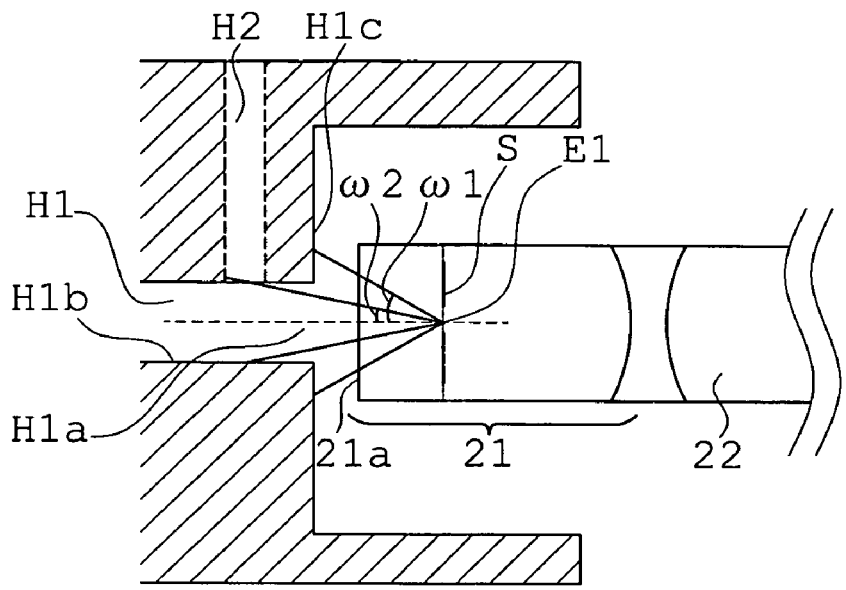
FIG. 4A is a principle diagram showing conceptually incidence light from an object.
Figure 4B:
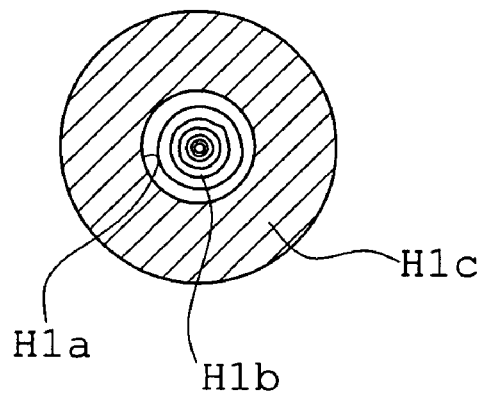
FIG. 4B is an explanatory diagram which illustrates a state of an image obtained when a pore having a smaller diameter than an outside diameter of an endoscope in a state shown in FIG. 4A.

FIG. 4 is an explanatory diagram in case that observation of a pore having a smaller diameter than an outside diameter of an endoscope using a conventional endoscope. FIG. 4A is a principle diagram showing conceptually incidence light from an object, and FIG. 4B is an explanatory diagram which illustrates an example of an image obtained when a pore having a smaller diameter than the outside diameter of an endoscope is observed in a state shown in FIG. 4A.

An endoscope 1 according to the present embodiment comprises a top part optical system 6 at the object side of the objective optical system 2 for endoscope in addition to constitution of a general conventional endoscope 5 such as an endoscope constituted with an objective optical system 2 for endoscope; an image transmission optical systems 3 such as a relay lens (in case of a rigid endoscope), an image guide fiber (in case of a flexible endoscope) and the like; and an image forming optical system 4 such as an eyepiece optical system or an image pick-up optical system equipped with CCD (in the example of FIG. 2, an example equipped with an eyepiece optical system is shown); or a video endoscope equipped with an objective optical system, and an image pick-up element such as CCD at the top part of it.

The objective optical system 2 for endoscope, has a lens group 21 with positive refracting power, a brightness aperture stop S, and a second lens group 22 with positive refracting power, where an incidence pupil E1 with the brightness aperture stop S is arranged at inside of the first lens group 21.

Figure 1:
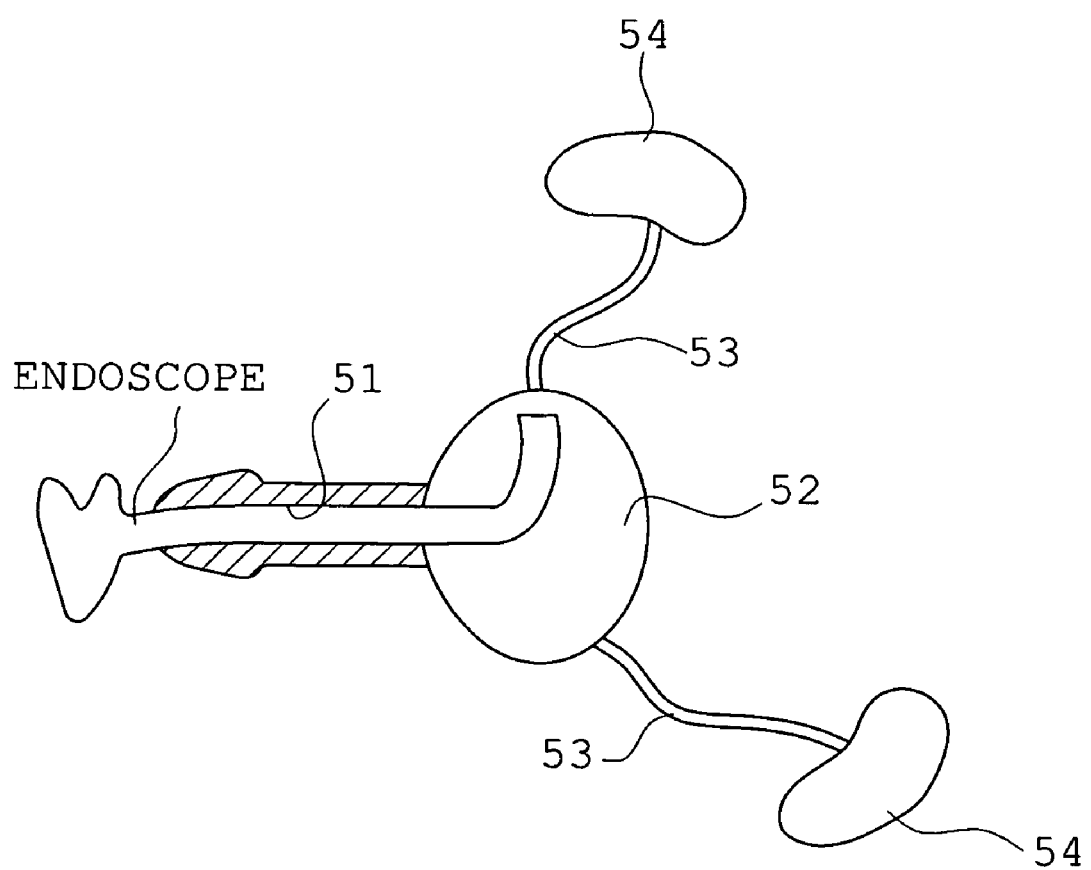
FIG. 1 is an explanatory diagram showing conceptually a state when a ureter is observed with an endoscope, as an example in which endoscope observation is carried out to the pore having a smaller diameter etc. than an outside diameter of the endoscope.

The top part optical system 6 is constituted as a relay lens optical system having lenses 61, 62, 63, 64, and 65, wherein an middle image Ia of an observation object (an illustration is not shown) is formed in the lens 63 arranged between the lens 62 and the lens 64, and an incidence pupil E2 which is conjugate to an incidence pupil E1 of the objective optical system for 2 endoscope is arranged at a position which is more projected toward the object side by a predetermined amount L than a surface M1 which is the utmost object side at the inside of the endoscope 1. In FIG. 1, S' is an image of the brightness aperture stop S which is formed at the incidence pupil E2.

Difference of an image obtained in case that a pore having a smaller diameter than an outside diameter of the endoscope is observed by using the endoscope 1 of the present embodiment in which the top part optical system 6 is arranged at the object side of the objective optical system 2 for endoscope, and an image obtained in another case by using the conventional endoscope 5 which does not have the top part optical system 6, will be explained.

Firstly, when an observation object is observed by using the endoscope 5 having the conventional objective optical system 2 for endoscope which does not have the top part optical system 6, the luminous flux from the observation object enters into a top surface 21a (a surface at the utmost object side in the endoscope 5) of the objective optical system 2 for endoscope in which the incidence pupil E1 is arranged at the inside (at a position of brightness aperture stops), indirection so that the luminous flux may approach to the optical axis.

As mentioned above, when a pore H1 having a smaller diameter than the outside diameter of the endoscope 5 is observed by using the endoscope 5 in which the luminous flux from the observation object enters into the top surface 21 in direction so that the luminous flux from the observation object may approach the optical axis, it is necessary to bring the top surface 21a of the objective optical system 2 for endoscope close to the entrance H1a of the pore H1 as much as possible, as shown in FIG. 4A, in order to enlarge an angle of incidence ω2 of the light which enters into the top surface 21a from the side wall H1b inside the pore H1 as much as possible.

However, even if it is constituted as mentioned above, the light from a perimeter H1c of an entrance H1a of the pore H1 will enter into the top surface 21a of the objective optical system 2 for endoscope in addition to the light from the side wall H1b of the pore H1. Here, as for the light which enters into the top surface 21a of the objective optical system 2 for endoscope from the observation object, the angle of incidence ω2 of the light which enters into the top surface 21a from the side wall H1b inside of the pore H1 having a smaller diameter than the diameter of the top surface 21a of the objective optical system 2 for endoscope becomes smaller than an angle of incidence ω1 of the light which enters into the top surface 21a from the perimeter H1c of the entrance H1a of the pore H1, and accordingly, an amount of information of the image obtained from the side wall H1b of the pore H1 will decrease.

Consequently, as shown in FIG. 4B, as for the perimeter H1c of the entrance of a pore H1, it can be observed with sufficient accuracy as an image is viewed from nearly front side. However, contrary to that, as to the side wall H1a inside of the pore H1, it cannot be observed with sufficient accuracy, since an image becomes an image having a large angle of incidence where the light enters slantingly with an angle, and accordingly, it is easy to overlook even if an abnormal part exists in the side wall H1b inside of the pore H1 and an inside of the pore H2 connected to the pore H1.

Contrary to this, the endoscope 1 of the present embodiment in which the top part optical system 6 is arranged at the object side of the objective optical system 2 for endoscope, is constituted such that by means of the top part optical system 6 arranged at the object side of the objective optical system for 2 endoscope, the middle image Ia of an observation object is formed in the lens 63 arranged between the lens 62 and the lens 64, and the incidence pupil E2 which is conjugate to the incidence pupil E1 of the objective optical system 2 for endoscope is arranged at the position which is projected toward the object side by a predetermined amount L than the surface M1 which is the utmost object side at the inside of the endoscope 1. In other words, it is constituted such that the incidence pupil E of the objective optical system 2 for endoscope is relayed at a position which is more projected by a predetermined amount L1 toward the object side than the surface M1 which is the utmost object side of the endoscope 1.

When an observation object is observed by using the endoscope 1 having such constitution, the luminous flux from the observation object is directed toward the center of the incident pupil E2 which is projected toward the object side by a predetermined amount L than the surface M1 which is the utmost object side at the inside of the endoscope 1. Then, after the luminous flux is crossed at the center, it enters into the surface M1 which is at the utmost object side inside of the endoscope 1 in a direction to which the luminous flux is separate from the optical axis.

Therefore, when the pore H1 having a smaller diameter than the outside diameter of the endoscope 1 is observed by using the endoscope 1 which has the objective optical system 2 for endoscope having the top part optical system 6 according to the present embodiment, as shown in FIG. 3A, by bringing the position of the incidence pupil E2 close to the entrance H1a of the pore H1, an angle of incidence of the light entering into the surface M1 which is at the utmost object side, from the side wall H1b inside of the pore H1 can be enlarged. Accordingly, light having the angle of incidence ω1' that is larger than ω1 (angle of incidence of the light from a range which was not able to be taken in as information of an image inside of the pore H1 in the conventional endoscope 1 shown in FIG. 4A) can be taken into the surface M1 which is at the utmost object side as an incidence light from the side wall H1b inside of the pore H1. Thus, an amount of information of the image obtained from the side wall H1b inside of the pore H1 increases. Consequently, as shown in FIG. 3B, as for the inside wall H1b inside of the pore H1, it can be observed with sufficient accuracy as an image viewed from nearly front side.

According to the endoscope 1 of the present embodiment, as mentioned above, the incidence pupil position E2 when the top part optical system 6 is attached, is located in a range up to a predetermined depth when the top surface of the top part optical system 6 is touched the perimeter H1c of the pore H1 near the entrance H1a of the pore H1. In this way, the side wall H1b inside of the pore H1 can be observed with sufficient accuracy, over a range of the predetermined depth. Consequently, it is easy to find an abnormal part when it exists in a side wall inside of the pore H1, or in an inside of the pore H2 connected to the pore H1. If the incidence pupil E2 is arranged so as to separate from the entrance of the pore H1 when the top part optical system 6 of the endoscope of the present embodiment is attached, the perimeter H1b of the pore H1 can be also observed with sufficient accuracy.

In the endoscope 1 of the present embodiment, the top part optical system 6 can be attached and detached to the objective optical system 2, as an adapter optical system for endoscope, or the top part optical system 6 and the objective optical system 2 can be integrated one. Further, when it is constituted such that the top part optical system 6 in the endoscope 1 of the present embodiment can be attached and detached to the objective optical system 2, it is desired that a light guiding means for guiding light emanated from the illumination optical system arranged around the objective optical system 2 for endoscope to an observation object is arranged in order that the top part optical system 6 does not interfere with illuminating light from the illumination optical system (illustration is not shown) which is generally arranged around the objective optical system 2. As a light guiding means, for example, a constitution in which cylindrical transparent material is arranged around a body tube holding the top part optical system 6, and a constitution in which a hole for passing light from an illumination optical system is formed on a part of the body tube are applicable.

In the present invention, since S' is not a substantial aperture stop, the light from all directions enters into the position of the middle image Ia. Therefore, when the light reflected on the side surface of the top portion optical system 6 enters in a regular optical path, flare is generated and the image quality decreases. Thus, it is desired that the lens 63 at the position of the middle image Ia is constituted to have a side surface as a surface with sand pattern having diffusivity for defusing the light entered into the side surface. Otherwise, the light which enters into the side surface may be absorbed and attenuated by applying black optical absorption material to the side surface the lens 63.

Furthermore, it is desirable to have a constitution such that lenses 62, 63, and 64 are joined in one, and a spacing pipe that may generate flare is not used.

From explanation mentioned above, it is evident that the present invention is useful in fields of medical treatment and industry in which observation of a side wall and the like inside a pore having smaller diameter than an outside diameter of an endoscope is demanded.

What is claimed is:

1. An endoscopic adapter optical system configured to be arranged on an object side of an endoscopic objective optical system that has, inside thereof, an entrance pupil,
   wherein, in a state where arranged on the object side of the endoscopic objective optical system, the endoscopic adapter optical system forms, at a position inside thereof, an intermediate image of an object, and relays the entrance pupil of the endoscopic objective optical system to a predetermined position that is closer to the object side than a most object-side surface of the endoscopic adapter optical system.

2. The endoscopic adapter optical system according to claim 1, wherein an optical element having a side surface with diffusivity is arranged at the position of the intermediate image.

3. The endoscopic adapter optical system according to claim 1, wherein an optical element having a side surface with light absorbing material is arranged at the position of the intermediate image.

4. An endoscope comprising:
an endoscopic objective optical system having, inside thereof, an entrance pupil; and
a top part optical system arranged on an object side of the endoscopic objective optical system,
wherein the top part optical system is configured to form, at a position inside thereof, an intermediate image of an object, and to relay the entrance pupil of the endoscopic objective optical system to a predetermined position that is closer to the object side than a most object-side surface of the top part optical system.

5. The endoscope according to claim 4, wherein an optical element having a side surface with diffusivity is arranged at the position of the intermediate image.

6. The endoscope according to claim 4, wherein an optical element having a side surface with light absorbing material is arranged at the position of the intermediate image.

* * * * *